US008926624B2

(12) United States Patent
Lee

(10) Patent No.: US 8,926,624 B2
(45) Date of Patent: Jan. 6, 2015

(54) BONE CEMENT INJECTION DEVICE

(75) Inventor: Sung-Woo Lee, Seoul (KR)

(73) Assignees: L & K Biomed Co., Ltd., Seoul (KR); Sung-Woo Lee, Seoul (KR)

( * ) Notice: Subject to any disclaimer, the term of this patent is extended or adjusted under 35 U.S.C. 154(b) by 0 days.

(21) Appl. No.: 13/617,509

(22) Filed: Sep. 14, 2012

(65) Prior Publication Data

US 2013/0006257 A1 Jan. 3, 2013

Related U.S. Application Data

(63) Continuation of application No. PCT/KR2010/004516, filed on Jul. 12, 2010.

(30) Foreign Application Priority Data

Mar. 15, 2010 (KR) ........................ 10-2010-0022844

(51) Int. Cl.
A61B 17/58 (2006.01)
A61B 17/34 (2006.01)
A61B 17/88 (2006.01)

(52) U.S. Cl.
CPC ......... *A61B 17/3472* (2013.01); *A61B 17/8805* (2013.01); *A61B 17/8811* (2013.01); *A61B 17/8819* (2013.01)
USPC ........................................................ 606/94

(58) Field of Classification Search
USPC .................................... 606/93, 94
See application file for complete search history.

(56) References Cited

U.S. PATENT DOCUMENTS

| 2006/0064101 | A1* | 3/2006 | Arramon .......................... 606/82 |
| 2006/0235417 | A1* | 10/2006 | Sala ................................ 606/79 |
| 2007/0010843 | A1 | 1/2007 | Green |
| 2007/0055283 | A1* | 3/2007 | Scribner et al. ................. 606/93 |
| 2007/0197935 | A1 | 8/2007 | Reiley et al. |
| 2007/0233146 | A1* | 10/2007 | Henniges et al. ............... 606/91 |
| 2007/0270876 | A1* | 11/2007 | Kuo et al. ....................... 606/92 |
| 2008/0269761 | A1 | 10/2008 | Truckai et al. |
| 2009/0157085 | A1 | 6/2009 | Melsheimer |

FOREIGN PATENT DOCUMENTS

KR 10-2009-0028436 A 3/2009

OTHER PUBLICATIONS

International Search Report for PCT/KR2010/004516 mailed Apr. 21, 2011.

* cited by examiner

*Primary Examiner* — Kevin T Truong
*Assistant Examiner* — Michael Araj
(74) *Attorney, Agent, or Firm* — Kramer Amado P.C.

(57) ABSTRACT

A bone cement injection device whereby bone cement is inserted through the skin and into bone, and can easily be separated during outflow of the bone cement into the blood vessels and spinal canal and curing. An outer insertion member has an outer needle tube having one end that is sharpened to be inserted through the skin and into bone and a partially closed part where the cross-sectional area of the internal space is reduced. A main hand grip is integrally formed on the other end of the outer needle tube and has a fastening part able to be fastened to a bone cement supply. An inner insertion member includes an inner needle rod for insertion into the other end part of the outer needle tube which opens through the main hand grip, and an auxiliary hand grip which is integrally formed on the inner needle rod.

5 Claims, 3 Drawing Sheets

BONE CEMENT INJECTION DEVICE

CROSS REFERENCE TO RELATED APPLICATIONS

This application is a continuation of and claims priority to International Patent Application No. PCT/KR2010/004516, filed Jul. 12, 2012, entitled "Bone Cement Injection Device", which claims priority to Korean Patent Application No. 10-2010-0022844, filed Mar. 15, 2010, the entire disclosures of both of which are hereby incorporated by reference in their entireties.

FIELD

The present invention relates to a bone cement injection device, and more specifically to a bone cement injection device which penetrates the skin to insert a bone cement into the bone, and stops injection of the bone cement when the bone cement has leaked into a blood vessel and spinal canal, and was hardening, and can be easily separated from the injected bone cement.

BACKGROUND

According to the related art, in the case that a bone cement should be injected into the bone due to a disease such as a vertebral compression fracture and a tumor formed in a vertebra, etc., a bone cement insertion operation is used.

Such a bone cement insertion operation is made through a device and operation process as follows.

First, a device including an outer needle tube and an inner needle rod with a sharp one end portion are partially inserted into the bone into which the bone cement is to be injected. Next, after separating the inner needle rod from the outer needle tube, the bone cement is supplied through the outer needle tube and the bone cement is again injected into the bone while pushing the inner needle rod into the outer needle tube at constant pressure.

However, if the bone cement is leaked into a blood vessel and spinal canal, complications such as paraplegia due to pulmonary embolism and spinal nerve damage may occur. Especially in the process of continuously observing using a radiation fluoroscope when injecting the bone cement, injection should be immediately stopped if there is a doctor's opinion of the bone cement leakage. At this time, the bone cement remaining in the outer needle tube also should not be injected. If the remaining bone cement is injected, the risk of complications such as pulmonary embolism and spinal nerve damage increases. At this time, if the outer needle tube is removed after the bone cement has hardened, the bone cement in the vertebra and the bone cement in the outer needle tube becomes one body, so the risk that the bone cement will remain in the muscle and skin tissue, which is an injection path, is high. Due to this, an operation for removing the bone cement should be performed, so the patient will have considerable physical and mental pain.

Also, bone cement has a considerably high hardening speed (hardens in about seven to ten minutes) and a high viscosity. Not only that, due to the friction with a narrow wall of the injection tube, it is sometimes difficult to complete the bone cement injection within the hardening time. Especially when bone cement hardens, it hardens as one body with the injection tube, so there is a problem that the bone cement that was already filled in the bone and the injection tube become one body to make it not easy to draw the tube out.

SUMMARY

Accordingly, to solve the above-mentioned problems, it is an object of the present invention to provide a bone cement injection device which penetrates the skin to insert a bone cement into the bone, and stops injection of the bone cement when the bone cement leaked into the blood vessel and spinal canal, and was hardening, and can be easily separated from the injected bone cement.

In order to accomplish the foregoing objects, according to an embodiment of the present invention, there is provided a bone cement injection device including: an outer insertion member including an outer needle tube having a sharp one end portion so as to be able to penetrate a skin to be inserted into a bone, and a main hand grip which is formed as one body at the other end portion of the outer needle tube and has a fastening portion for fastening with a bone cement supply means; and an inner insertion member including an inner needle rod which is inserted into the other end of the outer needle tube opened through the main hand grip, and a sub-hand grip formed as one body on the inner needle rod.

Preferably, the sub-hand grip is inserted into the main hand grip.

Preferably, the sub-hand grip has insert protrusions protruded on both sides, and the main hand grip has insert slots corresponding to the insert protrusions on the inside of the main hand grip.

Preferably, the main hand grip is formed in a U shape and has a fastening portion formed in a concave portion thereof so as to be protruded in the opposite direction of the outer needle tube.

Preferably, the fastening portion is a tubular shape having a male screw formed on the outer circumference portion, and an inner space of the fastening portion communicates with the outer needle tube.

Preferably, one end section of the inner needle rod is to have the same plane as one end section of the outer needle tube.

Preferably, the one end portion of the outer needle tube has a partially closed portion with a sectional area of an inner space partially reduced, and the one end portion of the inner needle rod has a closed tip of a shape corresponding to the partially closed portion of the outer needle tube.

According to the bone cement injection device of the present invention, it is possible to separate it easily and safely from the bone cement that was already injected into the bone, when the bone cement has leaked into a blood vessel and spinal canal, and was hardening, in the operation for inserting the bone cement into the bone by penetrating the skin. Also, it is possible to dramatically reduce the occurrence of complications caused by the leaking and hardening of the bone cement.

BRIEF DESCRIPTION OF THE DRAWINGS

The above objects, features and advantages of the present invention will become more apparent to those skilled in the related art in conjunction with the accompanying drawings. In the drawings.

DETAILED DESCRIPTION

Figure 1:
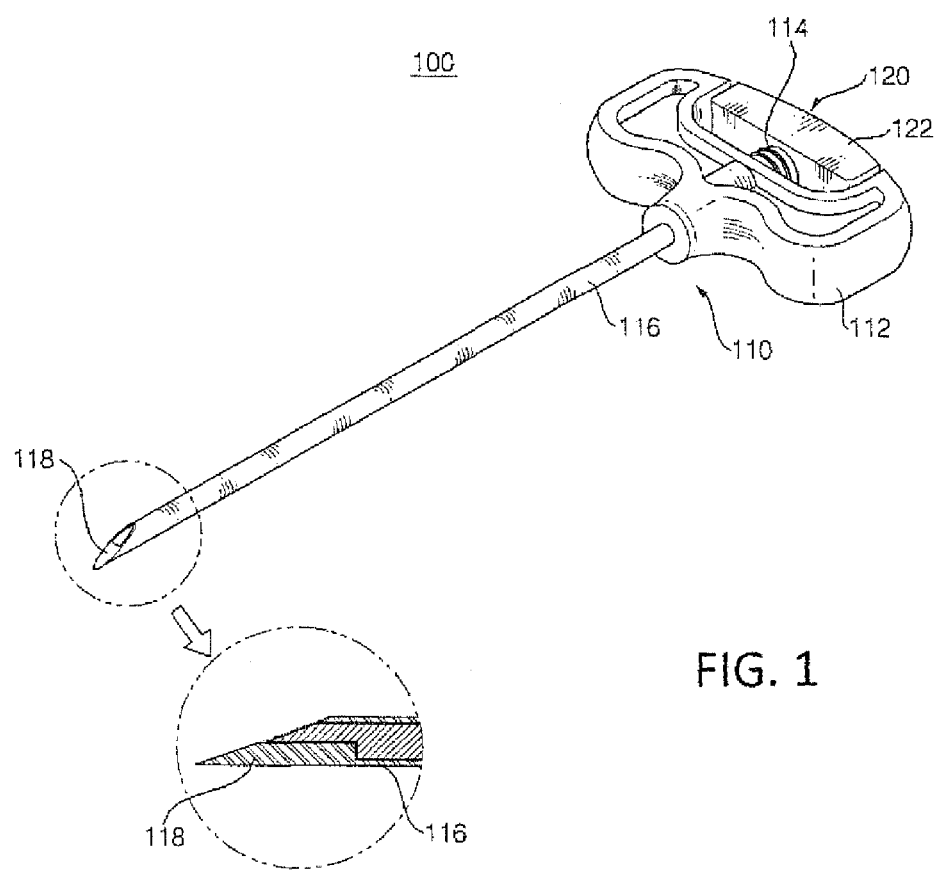
FIG. 1 is a perspective view of a bone cement injection device and a partially enlarged sectional view of the front end thereof according to an embodiment of the present invention.

Hereinafter, preferable embodiments of the present invention will be described with reference to the accompanying drawings. Referring to the drawings, wherein like reference characters designate like or corresponding parts throughout the several views. In the embodiments of the present invention, detailed description of the publicly known functions and configurations that are judged to be able to make the purport of the present invention unnecessarily obscure are omitted.

Figure 2:
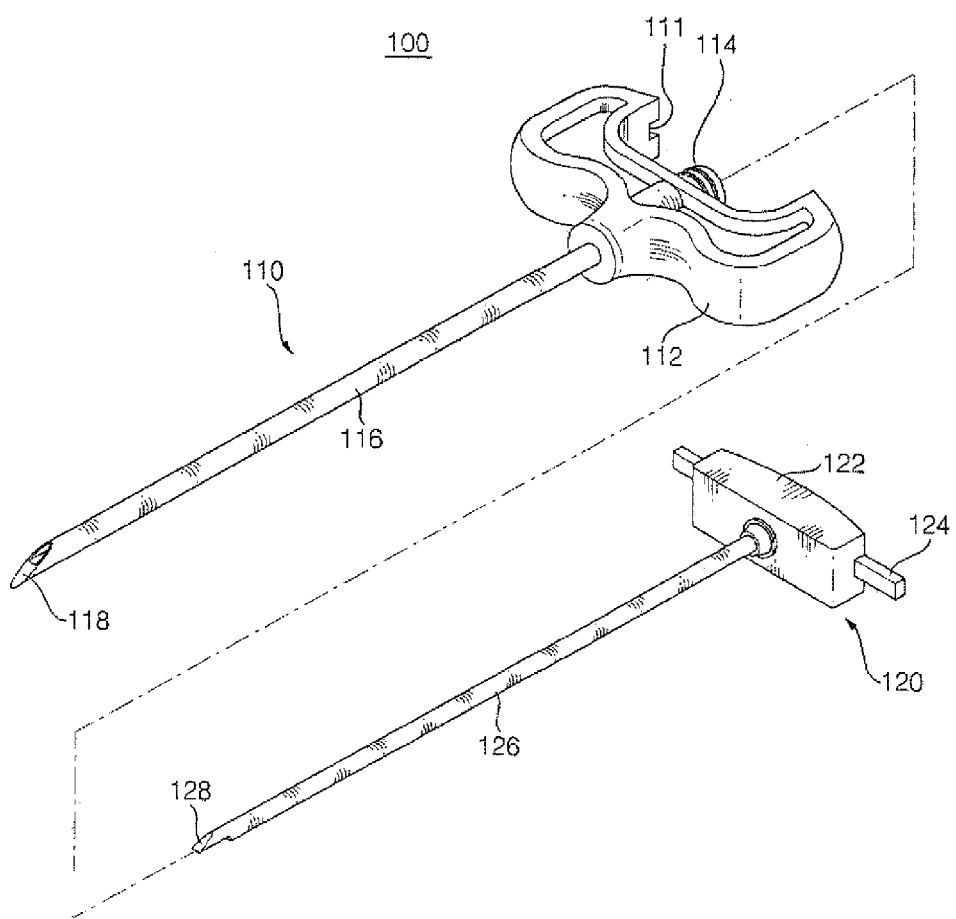
FIG. 2 is an exploded perspective view of the bone cement injection device of FIG. 1.

FIG. 1 is a perspective view of a bone cement injection device 100 and a partially enlarged sectional view of the front end thereof according to an embodiment of the present invention, and FIG. 2 is an exploded perspective view of the bone cement injection device 100.

The bone cement injection device 100 is configured substantially of two components of an outer insertion member 110 and an inner insertion member 120, as shown in FIG. 2.

The outer insertion member 110 includes a grippable main hand grip 112 and an outer needle tube 116 formed as one body with the main hand grip 112.

The main hand grip 112 is formed substantially in a U shape, and has a slot formed for the finger to be seated therein to enhance the grip feeling when the user grips it. In the U-shaped main hand grip 112 is formed, in protrusion, a fastening portion 114 on the bottom surface of the inside.

The fastening portion 114 is a portion fastened with a bone cement supply means 130. In the embodiment of the present invention, the fastening portion 114 is substantially a tube shape with its one end open, and a male screw is formed on the outer circumference portion.

In addition, the fastening portion 114 communicates with the inner space of an outer needle tube 116, so that bone cement can flow into the outer needle tube 116 through the bone cement supply means 130.

The outer needle tube 116 is fixed as one body to the main hand grip 112. The outer needle tube 116 is a tubular body with the cross section having a substantially tube shape, and its one end portion is formed sharply so as to penetrate the skin tissue and bone tissue, as shown in FIGS. 1 and 2. In the embodiment of the present invention, an end section of the outer needle tube 116 is formed in an acute angle to the lengthwise horizontal line of the outer needle tube 116 so as to make manufacture easy.

The inner insertion member 120 includes a sub-hand grip 122 for the user to grip, and an inner needle rod 126 formed as one body with the sub-hand grip 122.

The shape of the sub-hand grip 122 is not particularly limited, but it is necessary that the sub-hand grip 122 has such a structure, attachable to and detachable from the main hand grip 112, that the user can stably grip with the main hand grip 112 and the sub-hand grip 122 fastened to each other and the inner needle rod 126 does not make relative angular motion with respect to the outer needle tube 116.

For this, insert slots 111 are formed at a top end portion of the U shaped main hand grip 112. And on both sides of the sub-hand grip 122 are formed, in outward protrusion, insert protrusions 124 corresponding to the insert slots 111 so as to connect both top end portions of the U-shaped main hand grip 112 by the sub-hand grip 122. Especially by forming part or whole of the insert protrusion 124 a little large with respect to the insert slot 111, it is preferable that the fastening can be maintained without applying external force as the insert protrusions 124 are inserted in the insert slots 111.

It is preferable that the bottom face of the sub-hand grip 122 touches the top face of the fastening portion 114, so that impurities such as dust are not introduced into the inner space of the fastening portion 114 while the bone cement injection device 100 is stored.

The inner needle rod 126 that is formed as one body in the sub-hand grip 122 is inserted into the outer needle tube 116 through the fastening portion 114, and the one (front) end section of the inner needle rod 126 is to have the same plane as the one (front) end section of the outer needle tube 116. Accordingly, with the inner needle rod 126 inserted into the outer needle tube 116, the inner needle rod 126 occupies the inner space of the outer needle tube 116. As a result, when the bone cement injection device 100 penetrates the skin and bone, it can be prevented that a body tissue is introduced in through the front end of the outer needle tube 116.

Therefore, the one end section of the inner needle rod 126 should be in a closed state, and the inner needle rod 126 may be formed in a hollow tube to reduce the weight.

In the outer needle tube 116, the device should be separated from the skin and bone after bone cement is injected. In this case, one end portion of the outer needle tube 116 has a partially closed portion 118 with the sectional area of the inner space partially reduced so as to cut off the connection with the bone cement by force while the outer needle tube 116 is fixed with the bone cement by the hardening of bone cement.

Namely, when the bone cement is injected, a column-shaped structure, in which the bone cement remained in the outer needle tube 116 and the bone cement that has penetrated into the bone tissue become one body, is formed. Because of this, in the embodiment of the present invention, the space of one end portion of the outer needle tube 116 is reduced to become vulnerable to external force so that the column-shaped structure can be cut forcibly by external force.

The partially closed portion 118 is partially formed only at one end portion of the outer needle tube 116, so the inner space is suddenly reduced in one end portion. The partially closed portion 118 according to the embodiment of the present invention is formed in stepped protrusion inward of the inner wall of the outer needle tube 116 so that the space of the front end of the outer needle tube 116 becomes substantially a semi-circle.

Further, one end portion of the inner needle rod 126 has a closed tip 128 of a shape corresponding to the partially closed portion 118 so as to close the front end of the outer needle tube 116, as described above. Accordingly, the closed tip 128 has the cross section of a substantially semi-circle shape, and is formed stepped one end portion of the inner needle rod 126.

The bone cement injection device 100 according to the embodiment of the present invention is composed basically as described above. Hereinafter, how to use the bone cement injection device 100 will be described.

First, the initial state of the bone cement injection device 100 is a state in which the front end is closed as the inner needle rod 126 is inserted into the outer needle rod 116.

In this state, grip the main hand grip 112 having the sub-hand grip 122 fastened and pierce the skin with the front end of the device to penetrate into the bone tissue.

Figure 3:
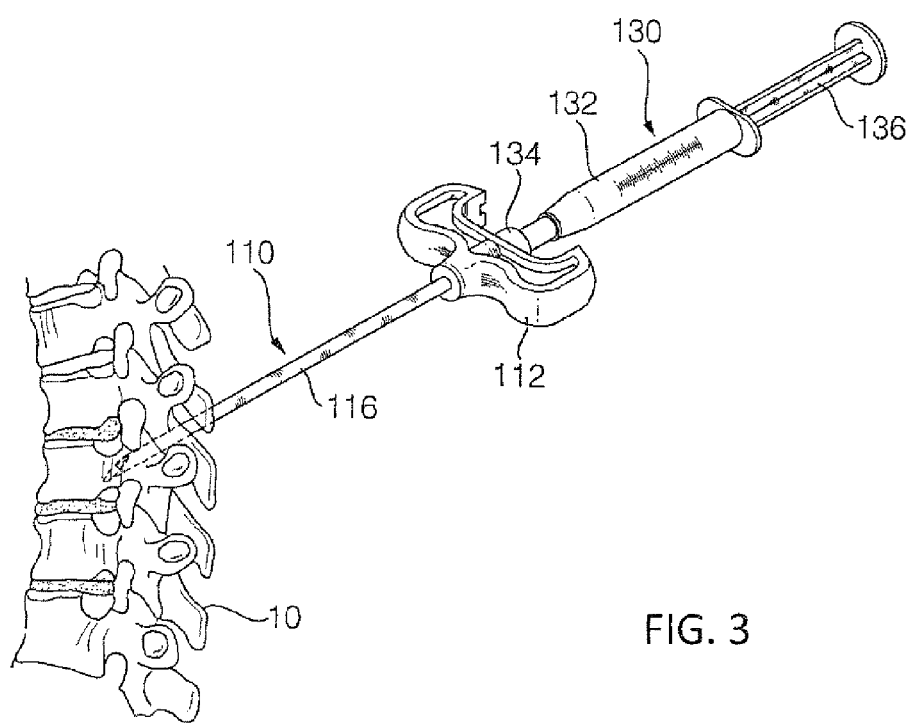
FIG. 3 is a perspective view schematically showing the bone cement injection device connected with the bone cement supply means after inserting one end portion of the bone cement injection device into the bone of FIG. 1.

Next, separate the sub-hand grip 122 from the main hand grip 112, and draw out the inner needle rod 126 in the outer needle tube 116 backward. In this state, connect a connector 134 of the bone cement supply means 130 to the fastening portion 114. The connector 134 has a female screw corresponding to the male screw of the fastening portion 114. FIG. 3 is a perspective view schematically showing the bone cement injection device 100 connected to the bone cement supply means 130 after inserting one end portion of the bone cement injection device 100 into the vertebra 10. The bone cement supply means 130 can use a conventional device known in the art, and it is not particularly limited.

After applying pressure by a pressing unit 136 to the bone cement that is in a cylinder 132 of the bone cement supply means 130, push the inner needle rod 126 into the outer needle tube 116 to inject the bone cement so as to supply the bone cement into the bone tissue through the inside of the outer needle tube 116.

Supply a given amount of bone cement, and when the bone cement is hardened, pull the main hand grip 112 to draw out the outer needle tube 116 from the bone tissue. At this time, the connected state of bone cement in the outer needle tube 116 that has become one body with the bone cement hardened in the bone tissue should be cut. For this, rotate the main hand grip 112 more than 180 degrees, so that the bone cement portion of the partially closed portion 118 is destroyed.

Therefore, it is possible to stably separate the outer needle tube 116 from the body tissue.

Although the present invention has been described in connection with the exemplary embodiments illustrated in the drawings, it is only illustrative. It will be understood by those skilled in the art that various modifications and equivalents can be made to the present invention. Therefore, the true technical scope of the present invention should be defined by the appended claims.

DESCRIPTION OF REFERENCE NUMERALS IN DRAWINGS

10: Vertebra, 100: Bone cement injection device
110: Outer insertion member, 111: Insert slot
112: Main hand grip, 114: Fastening portion
116: Outer needle tube, 118: Partially closed portion
120: Inner insertion member, 122: Sub-hand grip
124: Insert protrusion, 126: Inner needle rod
128: Closed tip, 130: Bone cement supply means
132: Cylinder, 134: Connector
136: Pressing unit

The invention claimed is:

1. A bone cement injection device comprising:
an outer insertion member including an outer needle tube having a sharp one end portion so as to be able to penetrate a skin to be inserted into a bone, and a main hand grip which is formed as one body at the other end portion of the outer needle tube and has a fastening portion for fastening with a bone cement supply means; and
an inner insertion member including an inner needle rod which is inserted into the other end of the outer needle tube opened through the main hand grip, and a sub-hand grip formed as one body on the inner needle rod,
wherein the inner needle rod has a flat end section that is substantially parallel to a flat end section of the outer needle tube,
the sharp one end portion of the outer needle tube has a partially closed portion with a sectional area of an inner space partially reduced wherein the sharp one end portion is formed in a stepped protrusion inward from an inner wall of the outer needle tube, and
the one end portion of the inner needle rod has a closed tip of a shape corresponding to the partially closed portion of the outer needle tube wherein the closed tip is formed in a stepped manner on one flat end section of the inner needle rod.

2. The device of claim 1, wherein the sub-hand grip is inserted into the main hand grip.

3. The device of claim 2, wherein the sub-hand grip has insert protrusions protruded on both sides, and the main hand grip has insert slots corresponding to the insert protrusions on the inside of the main hand grip.

4. The device of claim 1, wherein the main hand grip is formed in a U shape and has a fastening portion formed in a concave portion thereof so as to be protruded in the opposite direction of the outer needle tube.

5. The device of claim 4, wherein the fastening portion is a tubular shape having a male screw formed on the outer circumference portion, and an inner space of the fastening portion communicates with the outer needle tube.

* * * * *